United States Patent
Cass et al.

(10) Patent No.: US 6,300,543 B1
(45) Date of Patent: Oct. 9, 2001

(54) TRANSFORMATION OF ZYGOTE, EGG OR SPERM CELLS AND RECOVERY OF TRANSFORMED PLANTS FROM ISOLATED EMBRYO SACS

(75) Inventors: David D. Cass, Edmonton; Locksley E. McGann, Spruce Grove; Guichang Zhang, Richmond Hill; John D. Laurie, Edmonton, all of (CA); Jerome P. Ranch, West Des Moines; William J. Gordon-Kamm, Urbandale, both of IA (US)

(73) Assignees: Pioneer Hi-Bred International, Inc., Des Moines, IA (US); Govenors of the University of Alberta, Edmonton (CA)

( * ) Notice: Subject to any disclaimer, the term of this patent is extended or adjusted under 35 U.S.C. 154(b) by 0 days.

(21) Appl. No.: 09/147,489

(22) PCT Filed: Jul. 8, 1997

(86) PCT No.: PCT/US97/11184

§ 371 Date: May 12, 1999

§ 102(e) Date: May 12, 1999

(87) PCT Pub. No.: WO98/01576

PCT Pub. Date: Jan. 15, 1998

Related U.S. Application Data

(60) Provisional application No. 60/021,325, filed on Jul. 8, 1996.

(51) Int. Cl.$^7$ .............................. C12N 15/82; C12N 15/62; C12N 15/87; A01H 4/00
(52) U.S. Cl. ........................... 800/278; 800/300; 800/291; 800/320.1; 435/470; 435/418; 435/419; 435/69.8; 435/412; 435/424
(58) Field of Search ..................................... 435/419, 424, 435/468, 470, 412, 418, 69.8; 800/277, 278, 320, 320.1

(56) References Cited

U.S. PATENT DOCUMENTS 5,225,341  7/1993  Yoder et al. ...................... 435/172.3

FOREIGN PATENT DOCUMENTS

WO 94/00583 * 1/1994 (WO) .
WO 94/01999 * 2/1994 (WO) .

OTHER PUBLICATIONS

Ishida et al, 1996. High efficiency transformation of maize (*Zea mays* L.) mediated by *Agrobacterium tumefaciens*. Nature Biotechnol. 14:745–750.*
Desprez et al, 1995. Regeneration and characterization of plants produced from mature tobacco protoplasts via gametosomatic hybridization. Plant Cell Rep. 14:204–209.*
Kranz et al, 1991. In vitro fertilization of single, isolated gametes of maize mediated by electrofusion. Sex Plant Reprod. 4:12–16.*
Theunis et al, 1991. Isolation of male and female gametes in higher plants. Sex Plant Reprod 4:145–154.*
Rhodes et al, 1995. Transformation of maize by electroporation of embryos. In: Plant cell electroporation and electrofusion protocols, J.A. Nickoloff, ed, pp 121–131.
Zhang et al, 1998. Towards production of transgenic maize by microinjected exogenous DNA into zygotes and two-celled proembryos. In Vitro Cell and Devel Bio—Animal 34:68A.
Holm et al, 2000. Transformation of barely by microinjection into isolated zygote protoplasts. Transgenic Res. 9:21–32.
Matthys–Rochon et al, 1994. Isolation and microinjection of active sperm nuclei into egg cells and central cells of isolated embryo sacs. Zygote 2:29–35.
Campenot et al, 1992, *Zea mays* embryo sacs in culture I. Plant regeneration from 1 day after pollination embryos. Am. J. Bot. 79:1368–1373.
Roeckel et al, 1992. Plant transformation using the sexual route. Intl. Rev. Cytology 140:425–446.
Murai, et al., "Phaseolin Gene from Bean Is Expressed After Transfer to Sunflower Via Tumor–Inducing Plasmid Vectors", Science, vol. 222 476–482 (Nov. 1983).
Klein, et al., "Transformation of Microbes, Plants and Animals By Particle Bombardment", Biotechnology, vol. 10 286–291 (Mar. 1992).
Desprez, et al., "Regeneration and characterization of plants produced from mature tobacco pollen protoplasts via gametosomatic hybridization", Plant Cell Reports (1995) 14: 204–209.
Sanford, et al., "Delivery of Substances into Cells and Tissues Using a Particle Bombardment Process", Particulate Science and Technology 5:27–37 (1987).
An, et al., "Functional Analysis of the 3' Control Region of the Potato Wound–Inducible Proteinase Inhibitor II Gene", The Plan Cell, vol. 1, 115–122 (Jan. 1989).

(List continued on next page.)

Primary Examiner—David T. Fox
Assistant Examiner—Anne Kubelik
(74) Attorney, Agent, or Firm—Pioneer Hi-Bred International, Inc.

(57) ABSTRACT

Methodology is provided for the production of uniformly transformed plants capable of transmitting a foreign gene to progeny by sexual reproduction. A foreign gene is introduced into the zygote in an isolated embryo sac and a transformed plant is recovered. Alternatively, a foreign gene is introduced into an egg cell in an isolated embryo sac, the egg cell is fertilized with an isolated sperm cell and a transformed plant is recovered. Sperm cells may be transformed with a foreign gene, an egg cell in an isolated embryo sac is fertilized with the transformed sperm cells, or nuclei isolated from the transformed sperm cells, and a transgenic plant is recovered. Another method for the production of transgenic plants is transformation of an embryo in an isolated embryo sac. The transgenic plant produced by any one of these methods is homogeneously transformed and capable of transmitting the foreign gene to progeny by sexual reproduction.

6 Claims, 5 Drawing Sheets

OTHER PUBLICATIONS

Sanford, J., "The biolistic process", Tibtech, vol. 6, 299–302 (Dec. 1988).

Neuhaus, et al., "Transgenic rapeseed plants obtained by the microinjection of DNA into microspore–derived embryoids", Theor. Appl. Genet. (1987) 75:30–36.

Crameri, et al., "Improved Green Fluorescent Protein by Molecular Evolution Using DNA shuffling", Nature Biotechnology vol. 14, 315–319 (Mar. 1996).

Baker, et al., "Phenotypic assay for excision of the maize controlling element Ac in tobacco", The EMBO Journal 6:6 1547–1554 (1987).

Odell, et al., "Site–directed recombination in the genome of transgenic tobacco", Mol Gen. Genet, (1990) 223: 369–378.

Dale, et al., "Gene transfer with subsequent removal of the selection gene from the host genome", Proc. Natl. Acad. Sci USA, vol. 88, pp. 10558–10567 (Dec. 1991).

Knutzon, et al., "Modification of Brassica seed oil by antisense expression of a stearoyl–acyl carrier protein desaturase gene", Proc. Natl. Acad. Scit. USA, vol. 89, pp 2624–2628 (Apr. 1992).

Schena, et al., "A steroid–inducible gene expression system for plant cells", Proc. Natl. Acad. Sci. USA, vol. 88, pp. 10421–1425 (Dec. 1991).

Sengupta–Gopalan, et al., "Developmentally regulated expression of the bean β–phaseolin gene in tobacco seet", Proc. Natl. Acad. Sci. USA, vol. 82, p. 3320–3324 (May 1985).

Hiei, et al., "Efficient transformation of rice (*Oryza sativa* L.) mediated by Agrobacterium and sequence analysis of the boundaries of the T–DNA", The Plant Journal (1994) 6(2), 271–282.

Miki, et al., "Procedures for Introducing Foreign DNA into Plants", Methods in Plant Molecular Biology and Biotechnology CRC Press Chapter 6, pp. 67–68 (1993).

Gruber, et al., "Vectors for Plant Transformation", Methods in Plant Molecular Biology and Biotechnology, CRC Press, Phsiologia Plantarum 1962 vol. 15 FASC. 3 pp. 89–119.

Ishida, et al., "High efficiency transformation of maize (*Zea mays* L.) mediated by *Agrobacterium tumefaciens*", Nature Biotech vol. 14 745–750 (Jun. 1996).

Sanford, J., "Biolistic plant transformation", Physiologia Plantarum 79: 206–209, Copenhagen (1990).

Zhang, et al., "Efficient Transformation of Tobacco By Ultrasonication", J. of Biotechnology (Oct. 1991).

Deshayes, et al., "Liposome–mediated transformation of tobacco mesophyll protoplasts by an *Escherichia coli* plasmid", The EMBO Journal vol. 4 pp. 2731–2737 (1985).

Christou, et al., "Stable transformation of soybean by electroporation and root formation from transformed callus", Proc. Natl. Acad. Sci. USA, vol. 84 pp. 3962–3966 (Jun. 1987).

Hain, et al., "Uptake, integration, expression and genetic transmission of a selectable chimaeric gene by plant protoplasts", Mol. Gen. Genet., (1985) 199:161–168.

Draper, et al., "Ti Plasmid Homogous Sequences Present in Tissues from Agrobacterium Plasmid–transformed Petunia Protoplasts", Plant & Cell Physiol. 23(3): 451–458 (1982).

Fromm, et al., "Stable transformation of maize after gene transfer by electroporation", Nature vol. 391:27 pp 791–793 (Feb. 1986).

Luehrsen, et al., "Transient Gene Expression Assay by Electroporation of Maize Protoplasts", 109: 613–615 The Maize Handbook, Ed. Springer–Verlag (1993).

Laursen, et al., "Production of fertile transgenic maize by electroporation of suspension culture cells", Plant Molecular Biology 24: 51–61, (1994).

Crossway, et al., "Integration of foreign DNA following microinjection of tobacco mesophyll protoplasts", Mol. Gen. Genet. (1986) 202: 179–185.

Toyoda, et al., "Intranuclear microinjection for transformation of tomato callus cells", Plant Cell Reports, (1988) 7: 293–296.

Simmonds, et al., "Regeneration of Triticum aestivum apical explants after microinjection of germ line progenitor cells with DNA", Physiologia Plantarum, 85: 197–206, Copenhagen (1992).

Allington, P., The Experimental Manipulation of Ovule Tissues, Ed. G. P. Chapman (1985) "Micromanipulation of the unfixed cereal embryo sac", Chapter 4: 39–51.

Theunis, et al., "Isolation of male and female gametes in higher plants", Sex Plant Report (1991) 4: 143–154.

Wu, et al., "Enzymatic isolation of viable nucelli at the megaspore mother cell stage and in developing embryo sacs in *Nicotiana tabcum*", Sex Plant Report (1993) vol. 6:3 171–175.

Leduc, et al., "Deleterious effect of minimal enzymatic treatments on the development of isolated maize embryo sacs in culture", Sex Plant Reprod. (1995) 8:313–317.

Stiefel, et al., "Expression of a Maize Cell Wall Hydroxyproline–Rich Glycoprotein Gene in Early Leaf and Root Vascular Differentiation", The Plant Cell, vol. 2, 785–793 (Aug. 1990).

Kranz, et al., "In vitro fertilizationof single, isolated gametes of maize mediated by electrofusion", Sex Plant Reprod. (1991) 4:12–16.

Fraley, et al., "Expression of bacterial genes in plant cells", Proc. Natl. Acad. Sci. USA, vol. 80, pp. 4803–4807 (Aug. 1983).

van den Elzen, et al., "A chimaeric hygromycin resistance gene as a selectable marker in plant cells", Plant Molecular Biology, 5: 299–302, (1985).

Hayford, et al., "Development of a Plant Transformation Selection System Based on Expression of Genes Encoding Gentamicin Acetyltransferases", Plant Physiol., 86:4 1216–1222 (Apr. 1988).

Jones, et al., "A dominant nuclear streptomycin resistance marker for lant cell transformation", Mol. Gen. Genet., (1987) 210: 86–91.

Svab, et al., "Aminoglycoside-3" –adenyltransferase confers resistance to spectinomycin and streptomycin in *Nicotiana tabacum*, Plant Molecular Biology 14: 197–205 (1990).

Hille, et al., "Bleomycin resistance: a new dominant selectable marker for plant cell transformation", Plant Molecular Biology, 7: 171–176 (1986).

Eichholtz, et al., "Expression of Mouse Dihydrofolate Reductase Gene Confers Methotrexate Resistance in Transgenic Petunia Plants", Somatic Cell and Molecular Genetics, 13:1 67–76 (1987).

Shah, et al., "Engineering Herbicide Tolerance in Transgenic Plants", Science, vol. 233 pp. 478–481 (Jul. 1986).

Charest, et al., "In vitro study of transgenic tobacco expressing Arabidopsis wild type and mutant acetohydroxyacid synthase genes", Plant Cell Reports, (1990) 8:11 643–646.

De Greef, et al., "Evaluation of Herbicide Resistance in Transgenic Crops Under Field Conditions", Bio/technology, vol. 7 61–64 (1989).

Jefferson, R. "Assaying Chimeric Genes in Plants: The GUS Gene Fusion System", Plant Molecular Biology Reporter, vol. 5:4 387–405 (1987).

Teeri, et al., "Gene fusions to lacZ reveal new expression patterns of chimeric genes in transgenic plants", The EMBO Journal, 8:2 pp 343–350 (1989).

Koncz, et al., "Expression and assembly of functional bacterial luciferase in plants", Proc. Natl. Acad. Sci. USA, vol. 84 pp. 131–135 (Jan. 1987).

De Block, et al., "Expression of foreign genes in regenerated plants and in their progeny", The EMBO Journal vol. 3:8 pp. 1681–1689 (1984).

Ludwig, et al., "A Regulatory Gene as a Novel Visible Marker for Maize Transformation", Science, 247 pp. 449–450 (Jan. 1990).

Balzan, et al., "*Escherichia coli* iron superoxide dismutase targeted to the mitochondria of yeast cells protects the cells against oxidative stress", Proc. Natl. Acad. Sci. USA, vol. 92:4219–4223 (May 1995).

Conklin, et al., "Differential Accumulation of Antioxidant mRNAs in *Arabidopsis thaliana* Exposed to Ozone", Plant Physiol. (1995) 109:1 203–212.

Lyznik, et al., "Activity of yeast FLP recombinase in maize and rice protoplasts", Nucleic Acids Research, 21:4 969–975 (1993).

Lawson, et al., "Modification of the 5' untranslated leader region of the maize Activator element leads to increased activity in Arabidopsis", Mol. Gen. Genet. (1994) 245:5 608–615.

Heim, et al., "Engineering green fluorescent protein for improved brightness, longer wavelenghts and fluorescence resonance energy transfer", Current Biology, 6:2 178–182 (1996).

An, G. "Development of Plant Promoter Expression Vectors and Their Use for Analysis of Differential Activity of Nopaline Synthase Promoter in Transformed Tobacco Cells", Plant Physiol. (1986) 81:1 pp. 86–91.

Kay, et al., "Duplication of CaMV 35S Promoter Sequences Creates a Strong Enhancer for Plant Genes", Science, vol. 236 pp. 1149–1400 (Jun. 1987).

Ainley, et al., "Development of a heat shock inducible expression cassette for plants: Characterization of parameters for its use in transient expression assays", Plant Molecular Biology 14: 949–967 (1990).

Kares, et al., "IAA synthesis and root induction with iaa genes under ehat shock promoter control", Plant Molecular Biology, 15:2 225–236 (1990).

Kuhlemeier, et al., "The Pea rbcS–3A Promoter Mediates Light Responsiveness but not Organ Specificity", The Plant Cell, 1:4 471–478 (Apr. 1989).

Albani, et al., "A gene showing sequence similarity to pectin esterase is specifically expressed in developing pollen of *Brassica napus*. . . . pollen–specific promoters", Plant Molecular Biology, 16:4 501–513 (1991).

de Pater, et al., "Structure and expression of a root–specific rice gene", Plant Molecular Biology, 18:1 161–164 (1992).

Horsch, et al., "A simple and General Method for Transferring Genes into Plants", Science, 227: 1229–1231 (Mar. 1985).

Kado, et al., "Molecular Mechanisms of Crown Gall Tumorigenesis", Critical Reviews in Plant Sciences, 10(1): 1–32 (1991).

Moloney, et al., "High efficiency transformation of *Brassica napus* using Agrobacterium vectors", Plant Cell Reports, (1989) 8:4 238–242.

Mett, et al., "Copper–controllable gene expression system for whole plants", Proc. Natl. Acad. Sci. USA, 90:10 4567–4571 (May 1993).

Gatz, et al., "Regulation of a modified CaMV 35S promoter by the Tn10–encoded Tet repressor in transgenic tobacco", Mol. Gen. Genet. (1991) 227:2 229–237 (1991).

Röder, et al., "Efficiency of the tetracycline–dependent gene expression system: complete suppression and efficient induction of the rolB phenotype in transgenic plants", Mol. Gen. Genet. (1994) 243:1 pp. 32–38.

Simpson, et al., "Light–inducible and tissue–specific expression of a chimaeric gene under control of the 5'–flanking sequence of a pea chlorophyll a/b–binding protein gene", The EMBO Journal, 4:11 2723–2729 (1985).

Timko, et al., "Light regulation of plant gene expression by an upstream enhancer–like element", Nature 318:6046 579–582 (Dec. 1985).

Twell, et al., "Isolation and expression of anther–specific gene from tomato", Mol. Gen. Genet. (1989) 217:2/3 240–245.

Guerrero, et al., Promoter sequences from a maize pollen–specific gene direct tissue–specific Mol. Gen. Genet. (1990) 224:2 161–168.

Twell, et al., "Activation and developmental regulation of an Arabidopsis anther–specific promoter in microspores and pollen of *Nicotiana tabacum*", Sexual Plant Reproduction, 6:4 217–224 (1993).

Odell, et al., "Identification of DNA sequences required for activity of the cauliflower mosaic virus 35S promoter", Nature, 313 pp. 810–812 (Feb. 1985).

McElroy, et al., "Isolation of an Efficient Actin Promoter for Use in Rice Transformation", The Plant Cell, 2:2 163–171 (Feb. 1990).

Christensen, et al., "Sequence analysis and transcriptional reulation by heat shock of polyubiquitin transcripts from miaze", Plant Molecular Biology, 12:6 619–632 (1989).

Christensen, et al., "Maize polyubiquitin genes: structure, thermal perturbation of expression . . . following transfer to protoplasts by electroporation", Plant Mol. Biol., 18:4 675–689 (1992).

Last, et al., "pEmu: an improved promoter for gene expression in cereal cells", Theor. Appl. Genet., (1991) 81:5 581–588.

Velten, et al., "Isolation of a dual plant promoter fragment from the Ti plasmid of *Agrobacterium tumefaciens*", The EMBO Journal, 3:12 2723–2730 (1984).

Lepetit, et al., "A plant histone gene promoter can direct both replication–dependent and –independent gene expression in transgenic plants", Mol. Gen. Genet., (1992) 231:2 276–285.

Atanassova, et al., "A 126 bp fragment of a plant histone gene promoter confers preferential expression in meristems of transgenic arabidopsis", The Plant Journal, (1992) 2(3) 291–300.

Becker, et al., "The cab–m7 gene: a light–inducible, mesophyll–specific gene of maize", The Molecular Biology, 20: 49–60 (1992).

Knox, et al., "Structure and organization of two divergent α–amylase genes from barley", Plant Molecular Biology, 9: 3–17 (1987).

Lerner, et al., "Cloning and Characterization of Roote-Specific Barley Lectin", Plant Physiol, (1989) 91, 124–129.

Fontes, et al., "Characterization of an Immunoglobulin Binding Protein Homolog in the Maize floury–2 Endosperm Mutant", The Plant Cell, vol. 3, 483–496 (May 1991).

Matsuoka, et al., "Propeptide of a precursor to a plant vacuolar protein required for vaculolar targeting", Proc. Natl. Acad. Sci. USA, vol. 88 pp. 834–838 (Feb. 1991).

Gould, et al., "A Bonserved Tripeptide Sorts Proteins to Peroxisomes", J. of Cell Biology, 108:5 1657–1664 (May 1989).

Creissen, et al., "Molecular characerization of glutathione reductase cDNAs from pea (*Pisum sativum* L.)", The Plant Journal, (1991) 2(1), 129–131.

Murashige, et al., "A Revised Medium for Rapid Growth and Bio Assays with Tobacco Tissue Cultures", Physiologia Plantarum, vol. 15, 473–497 (1962).

Campenot, et al., "*Zea mays* Embryo Sacs In Culture. I. Plant Regneration From 1 Day After Pollination Embryos", American J. of Botany, 79:12 1368–1373 (1992).

"Positions Availble", Plant Molecular Biology Reporter, vol. 5, (3) 357–358 (1987).

Spurr, A., "A Low–Viscosity Epoxy Resin Embedding Medium for Electron Miscroscopy", J. Ultrastructure Research, 26, 31–43 (1969).

Zhang, et al., "Kinetics of Aluminum Uptake in *Triticum aestivum* L.", Plant Physiol. (1990) 94, 577–584.

Christensen, et al., "Maize polyubiquitin genes: strucure, thermal perturbation of expression and transcript splicing . . . following transfer to protoplasts by electroporation", Plant Molecular Biology, 18: 675–689 (1992).

Jefferson, et al., "GUS fusions: β–glucuronidase as a sensitive and versatile gene fusion marker in higher plants", The EMBO Journal, 6:13 pp. 3901–3907 (1987).

Vacanneyt, et al., Construction of an intron–containing marker gene: Splicing of the intron in transgenic plants and its use in monitoring early events in Agrobacterium–mediated plant transformation, Mol. Gen. Genet. (1990) 220: 245–250.

Gallie, et al., "The 5'–leader sequence of tobacco mosaic virus RNA enhances the expression of foreign gene transcripts in vitro and in vivo", Nucleic Acids Research, 15:8 3257–3273 (1987).

Dennis, et al., "Molecular analysis of the alcohol dehydrogenase (Adhl) gene of maize", Nucleic Acids Research, 12:9 2983–4001 (1984).

White, et al., "A cassette containing the bar gene of *Streptomyces hygroscopicus*: a selectable marker for plant transformation", Nucleic Acids Research, 18:4 p. 1062 (1990).

Mogensen, et al., "Dynamics of Nuclear DNA Quantities during Zygote Development in Barley", The Plant Cell, 7:4 487–494 (1995).

Close, P., "Cloning and Molecular Characterization of Two Nuclear Genes for *Zea mays* Mitochondrial Chaperonin 60", Dissertation: Iowa State University, (1993) 1–218.

* cited by examiner

TRANSFORMATION OF ZYGOTE, EGG OR SPERM CELLS AND RECOVERY OF TRANSFORMED PLANTS FROM ISOLATED EMBRYO SACS

CROSS-REFERENCE TO RELATED APPLICATION

This application is a 371 of PCT/US97/11184, filed Jul. 8, 1997, which claims the benefit of U.S. Provisional Application Ser. No. 60/021,325, filed Jul. 8, 1996, herein incorporated by reference.

BACKGROUND OF THE INVENTION

1. Field of the Invention

The present invention relates to a method of plant transformation in which a foreign gene is introduced into the zygote in an isolated embryo sac and a transgenic plant is recovered. The present invention also relates to a plant-transformation approach whereby a foreign gene is introduced into an egg cell in an isolated embryo sac, the egg cell is fertilized with a sperm cell, and a transgenic plant is recovered. In addition, the present invention relates to plant transformation by introducing a foreign gene into isolated sperm cells, after which a transformed sperm cell, or the nucleus isolated from the transformed sperm cell, is fused with an egg in an isolated embryo sac and a transgenic plant is recovered. These methodologies yield uniformly transformed plants capable of transmitting a foreign gene to progeny.

2. Background

Numerous methods for plant transformation have been developed, including biological and physical plant transformation protocols. See, for example, Miki et al., "Procedures for Introducing Foreign DNA into Plants" in METHODS IN PLANT MOLECULAR BIOLOGY AND BIOTECHNOLOGY 67–88 (CRC Press, 1993). In addition, expression vectors and in vitro culture methods for plant cell or tissue transformation and recovery of plants are available. See, for example, Gruber et al., "Vectors for Plant Transformation," loc. cit. at 89–119.

Production of transgenic plants first became routine through the use of Agrobacterium. The host range for Agrobacterium-mediated transformation is broad and includes not only dicotyledonous but also monocotyledonous plants such as rice and maize. Hiel et al., *The Plant Journal* 6: 271–282 (1994) and Ishida et al., *Nature Biotechnol.* 14: 745–750 (1996). Several methods of plant transformation, collectively referred to as "direct gene transfer," have been developed as an alternative to Agrobacterium-mediated transformation.

A generally applicable method of plant transformation is microprojectile-mediated transformation wherein DNA is carried on the surface of microprojectiles measuring 1 to 4 $\mu$m. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5: 27 (1987); Sanford, *Trends Biotechnol.* 6: 299 (1988); Sanford, *Physiol. Plant* 79: 206 (1990); Klein et al., *Bio/Technology* 10: 268 (1992).

Another method for physical delivery of DNA to plants is sonication of target cells. Zhang et al., *Bio/Technology* 9: 996 (1991). Alternatively, liposome or spheroplast fusion have been used to introduce expression vectors into plants. Deshayes et al., *EMBO J.* 4: 2731 (1985); Christou et al., *Proc Nat'l Acad. Sci. U.S.A.* 84: 3962 (1987). Direct uptake of DNA into protoplasts using $CaCl_2$ precipitation, polyvinyl alcohol, poly-L-ornithine or electroporation have also been reported. Hain et al., *Mol. Gen. Genet.* 199: 161 (1985); Draper et al., *Plant Cell Physiol.* 23: 451 (1982); Fromm et al., *Nature* 319; 791 (1986). Electroporation of protoplasts and plant cells in intact tissue is well documented. Luehrsen et al., in THE MAIZE HANDBOOK 613–615, Freeling et al. (eds.) (1994); deHalluin et al., *Plant Cell* 4: 1495–1505 (1992); Laursen et al., *Plant Mol. Biol.* 24: 51–61 (1994).

Finally, microinjection of DNA has been studied in a variety of plant cells including, for example, isolated protoplasts, callus, microspore-derived embryonic cells and apical meristem. Crossway et al., *Mol. Gen. Genet.* 202: 179–185 (1986); Toyoda et al., *Plant Cell Rep.* 7: 293–296 (1988); Neuhaus et al. *Theor. Appl. Genet.* 75: 30–36 (1987); Simmonds et al., *Physiol. Plantarum* 85: 197–206 (1992).

Although the production of gametes and zygotes by plants is well-understood, reproducible methods for in vitro manipulation and transformation of these cells are needed. In most plant species, embryo sacs are deeply enclosed in the sporophytic tissues and therefore the embryo sacs are difficult to manipulate. Microsporocytes and developing pollen grains are also embedded in sporophytic tissues.

Within the immature anther are cavities containing microsporocytes or pollen mother cells. Each mother cell undergoes two successive nuclear divisions to form a tetrad of four microspores. Each of these microspores may develop into a pollen grain. A microspore develops into a pollen grain by a thickening of the spore wall and a division of the microspore nucleus to form a vegetative cell and a generative cell.

Pollination involves the transfer of pollen from anther to stigma. Pollen germinates on the stigma and a pollen tube grows through the style and enters the tip of the ovule through the micropyle. Two male gametes or sperm cells are formed by division of the generative cell of the pollen grain. The sperm cells move through the pollen tube and are emptied into the embryo sac.

Within each ovule is a megasporocyte that undergoes two successive nuclear divisions to produce four megaspores. Three of the megaspores usually disintegrate while the fourth continues to undergo nuclear divisions and forms an eight nucleate embryo sac. The egg and two synergids are found near the micropyle while three nuclei are found on the opposite end of the embryo sac. Two polar nuclei remain in the center of the embryo. One sperm cell fuses with the egg cell to form the zygote which eventually develops into the embryo and a new plant. The second sperm fuses with the two polar nuclei to form the primary endosperm nucleus which divides many times to form the endosperm.

Methods for the isolation of living embryo sacs have been developed for plant species by using either micromanipulation or enzymatic digestion. Allington, "Micromanipulation of the Unfixed Cereal Embryo Sac," in THE EXPERIMENTAL MANIPULATION OF OVULE TISSUES 39–51 (Longman, N.Y., 1985); Theunis et al., *Sex Plant Reprod.* 4: 145–154 (1991); Wu et al., loc. cit. 6: 171–175 (1993). In vitro manipulation of fertilized embryo sacs frequently results in low viability or production of abnormal embryos. Leduc et al., loc. cit. 8: 313–317 (1995).

Many plant transformation systems, especially for cereals, involve callus-based selection protocols and extensive in vitro culturing. These methodologies are time consuming and increase the likelihood that somaclonal variants will arise that exhibit undesirable agronomic characteristics.

Use of developmentally organized explants as targets for transformation circumvent time-consuming tissue culture steps but increases the likelihood that chimeric plants are produced.

Targeting gametes, zygotes or early stage embryos in embryo sacs for transformation is a potential solution to these problems. Transformed plants can be rapidly recovered thereby eliminating the need for a prolonged tissue culture step. The method thereby circumvents classical somatic tissue culture. Instead, the method permits recovery of transformed plants through normal embryogenesis. In addition, transformed gametes and zygotes, as well as a high percentage of early stage embryos, will give rise to uniformly transformed plants capable of transmitting the foreign gene to progeny.

A need therefore exists for an efficient method for production of transgenic plants uniformly transformed with a foreign gene. A need also exists for an efficient method for production of transformed plants capable of transmitting a foreign gene to progeny. A further need exists for a method of isolating embryo sacs that permits zygote development into an embryo which will develop into a normal whole plant. In addition, a need exists for a method for the transformation of gamete cells or zygotes.

SUMMARY OF THE INVENTION

Accordingly, it is an object of the present invention to provide a method for production of plants that are uniformly transformed with a foreign gene but which does not involve prolonged in vitro culture.

Another object of the present invention is to provide an efficient method for production of transformed plants capable of transmitting a foreign gene to progeny.

These and other objects are achieved, in accordance with one embodiment of the present invention, by the provision of a method for producing a transformed plant, comprising the steps of (a) isolating an embryo sac from a plant; (b) introducing an expression vector carrying a foreign gene into the zygote or embryo in said embryo sac; and then (c) recovering a transformed plant from said zygote or embryo.

In another embodiment of the present invention, step (b) of the method for producing a transformed plant comprises (i) introducing an expression vector carrying said foreign gene into the egg cell of said isolated embryo sac; and then (ii) fertilizing said transformed egg cell with a plant sperm cell isolated from said plant, to produce said zygote or embryo.

In yet another embodiment of the present invention, step (b) comprises fertilizing the egg cell in said isolated embryo sac with a plant sperm cell that contains an expression vector carrying a foreign gene, to produce said zygote or embryo.

In another embodiment of the present invention, step (b) comprises (i) introducing an expression vector carrying a foreign gene into sperm cells from a plant; (ii) isolating nuclei from said transformed sperm cells; and (iii) fertilizing the egg cell in said isolated embryo sac with said isolated nuclei, to produce said zygote or embryo. The method of the present invention is used to produced transgenic monocots, such as cereals, and most preferably transgenic maize.

DETAILED DESCRIPTION OF PREFERRED EMBODIMENTS

Definitions

Figure 1A:
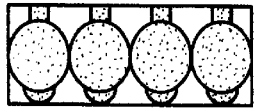
FIGS. 1A–1C show the orientation of ovaries on the specimen blocks prior to sectioning on the Vibratome: (a) top view, (b) front view and (c) side view.

In the description that follows, a number of terms are used extensively. The following definitions are provided to facilitate understanding of the invention.

An embryo sac is typically an eight-nucleate female gametophyte. The embryo sac arises from the megaspore by successive mitotic divisions.

A megaspore is one of the four haploid spores originating from the meiotic division of the diploid megaspore mother cell in the ovary and which gives rise to the megagametophyte.

A microspore is one of the four haploid spores originating from the meiotic division of the diploid microspore mother cell in the anther and which gives rise to the pollen grain.

The polar nuclei are two centrally located nuclei in the embryo sac that unite with the second sperm in a triple fusion. In certain seeds the product of this triple fusion develops into the endosperm A structural gene is a DNA sequence that is transcribed into messenger RNA (mRNA) which is then translated into a sequence of amino acids characteristic of a specific polypeptide.

A promoter is a DNA sequence that directs the transcription of a structural gene. Typically, a promoter is located in the 5-prime region of a gene, proximal to the transcriptional start site of a structural gene. If a promoter is an inducible promoter, then the rate of transcription increases in response to an inducing agent. In contrast, the rate of transcription is not regulated by an inducing agent if the promoter is a constitutive promoter. Also, the promoter may be regulated in a tissue-specific or tissue-preferred manner such that it is only active in transcribing the associated coding region in a specific tissue type(s) such as leaves, roots or meristem.

A cytoplasmically localized protein is a protein coded for by a gene which does not include any specific signal for targeting of the protein into any subcellular organelle or compartment or any signals for secretion of the protein. For example, the GFP structural gene operably linked 5-prime to a promoter and to an appropriate 3-prime sequence encodes for a protein compartmentalized in the cytoplasm.

A signal or targeting sequence is a structural peptide domain required for targeting of a given polypeptide to a subcellular organelle, subcellular compartment or secretion from the cell. As used herein, the phrase sequence for subcellular localization is intended to refer collectively to any form of signal., targeting or retention sequence as defined herein. Signal sequences for a polypeptide directed to the chloroplast or mitochondrion are largely localized to the amino-terminus of the polypeptide. Signal sequences for a polypeptide directed to the glyoxysomes and peroxisomes are largely localized to the carboxy-terminal domains of the polypeptide. Accordingly, targeted transport of the GFP protein is accomplished by means of chemically joining in proper reading frame, or operably linking, the nucleotide sequence encoding a signal sequence to the 5-prime and/or 3-prime region of the GFP structural gene.

A mitochondrial targeting sequence facilitates the transport of a protein to a mitochondrial compartment. Typically, the mitochondrial targeting sequence is located at the amino-terminus of a polypeptide.

A secretion targeting sequence targets a polypeptide for export into the extracellular space through the ER. For example, operably linking a nucleotide sequence encoding the barley alpha amylase 1 (BAA) secretory targeting sequence to the 5-prime end of a structural gene targets the encoded protein for export into the extracellular space.

A cell wall targeting sequence targets a polypeptide for export from the cell but the polypeptide is specifically localized to the cell wall. For example, cell wall localization of a polypeptide is accomplished by operably linking a nucleotide sequence encoding BAA 5-prime, and operably linking a nucleotide sequence encoding a portion of the maize hydroxyproline-rich glycoprotein 3-prime to a gene encoding the polypeptide. Steifel et al., *Plant Cell* 2: 785–793 (1990).

A vacuolar signal sequence facilitates the transport of a protein to the vacuole. For example, vacuolar targeting is accomplished by fusing the BAA secretory signal sequence at the amino-terminus of the protein and a sequence encoding a vacuolar signal sequence to the carboxy-terminus. Transport of a polypeptide to the vacuole is therefore accomplished by means of operably linking a nucleotide sequence encoding BAA 5-prime, and a nucleotide sequence encoding a vacuolar signal sequence 3-prime to a gene encoding a polypeptide. Alternatively, vacuolar targeting is accomplished by constructing a nucleotide sequence comprising in the 5-prime to 3-prime direction nucleotide sequences encoding a vacuole signal sequence, BAA and a polypeptide.

An endoplasmic reticulum retention sequence targets a polypeptide for localization in the lumen of the endoplasmic reticulum. For example, a polypeptide is targeted for retention in the endoplasmic reticulum through the addition of the BAA sequence on the amino-terminus and an endoplasmic reticulum signal sequence on the carboxy-terminus of the polypeptide.

A nuclear targeting sequence facilitates transport of a polypeptide to the nucleus. Typically, the nuclear signal sequence is located at the amino-terminus of a polypeptide. In order to retain the nuclear targeted protein in the nucleus, it may be necessary to increase the molecular weight of the protein by means of fusing an unrelated protein to the carboxy-terminus of the targeted protein. For example, GFP was retained in the nucleus by operably linking a nucleotide sequence encoding a nuclear signal sequence 5-prime and a nucleotide sequence encoding maize acetolactate synthase 3-prime to a gene encoding a polypeptide.

A peroxisomal targeting sequence facilitates the transport of a polypeptide into the peroxisome. Typically, the peroxisomal signal sequence is a tripeptide located at the carboxy-terminus of a polypeptide.

A chloroplast targeting sequence facilitates the transport of a nuclear encoded protein to a chloroplast compartment. Typically, the chloroplast signal sequence is located at the amino-terminus of a polypeptide. Accordingly, transport of a polypeptide to a chloroplast compartment is accomplished by means of operably linking the nucleotide sequence encoding a chloroplast signal sequence to the 5-prime region of a gene encoding a polypeptide.

An isolated DNA molecule is a DNA that is not integrated in the genomic DNA of an organism. An isolated DNA molecule is a chemically-synthesized DNA molecule that is not integrated in the genomic DNA of an organism.

Complementary DNA (cDNA) is a single-stranded DNA molecule that is formed from an mRNA template by the enzyme reverse transcriptase. Typically, a primer complementary to portions of mRNA is employed for the initiation of reverse transcription. Those skilled in the art also use the term "cDNA" to refer to a double-stranded DNA molecule consisting of such a single-stranded DNA molecule and its complementary DNA strand.

The term "expression" refers to the biosynthesis of a gene product. For example, in the case of a structural gene, expression involves transcription of the structural gene into mRNA and the translation of mRNA into one or more polypeptides.

A cloning vector is a DNA molecule, such as a plasmid, cosmid, or bacteriophage, that has the capability of replicating autonomously in a host cell. Cloning vectors typically contain one or a small number of restriction endonuclease recognition sites at which foreign DNA sequences can be inserted in a determinable fashion without loss of an essential biological function of the vector, as well as a marker gene that is suitable for use in the identification and selection of cells transformed with the cloning vector. Marker genes typically include genes that provide tetracycline resistance or ampicillin resistance.

An expression vector is a DNA molecule comprising a gene that is expressed in a host cell. Typically, gene expression is placed under the control of certain regulatory elements, including constitutive or inducible promoters, tissue-specific regulatory elements, and enhancers. Such a gene is said to be operably linked to the regulatory elements.

Transformation includes introduction of genetic material into plant cells resulting in chromosomal integration and stable heritability through meiosis. Transformation also includes introduction of genetic material into plant cells in the form of plant viral vectors involving epichromosomal replication and gene expression which may exhibit variable properties with respect to meiotic stability.

A foreign gene refers in the present description to a DNA sequence that is operably linked to at least one heterologous regulatory element. A plant is uniformly transformed with a foreign gene if each somatic cell in the plant carries at least one copy of the gene integrated into the plant chromosome.

A recombinant host may be any prokaryotic or eukaryotic cell that contains either a cloning vector or expression vector. This term also includes those prokaryotic or eukaryotic cells that have been genetically engineered to contain the cloned gene(s) in the chromosome or genome of the host cell.

A transgenic plant is a plant having one or more plant cells that contain an expression vector.

A green fluorescent protein (GFP), as well as a functional fragment of a GFP, is capable of producing a green fluorescence. GFP absorbs in the UV to blue range with a peak at 395 nm and emits in the green with a peak at 510 nm. $GFP_m$ is a nucleotide sequence coding for GFP in which the DNA sequence has been modified based on codon preference in maize. The nucleotide sequence of $GFP_m$ is shown in co-pending U.S. patent application Ser. No. 60/016,345, now WO97/41228, which is incorporated herein by reference.

Plant embryo sacs are isolated by sectioning ovule tissue. Intact plant embryo sacs that can be utilized for in vitro transformation and plant recovery are obtained by serially sectioning ovaries. The thickness of the sections varies from species to species depending on the size of the ovule. For example, the thickness of sections for maize is in the range of 250 to 300 µm. The isolated ovary sections contain embryo sacs surrounded by nucellus and the ovary wall. The structural integrity of the embryo sacs is maintained by this method of isolation. Intact embryo sacs are contained between thin layers of nucellus and are clearly visible using the stereomicroscope. The egg apparatus is visible, showing the egg cell and the two synergids. In addition, antipodal cells are visible. The sections containing the embryo sacs can be readily manipulated with forceps.

The plant embryo sacs isolated by the method of the present invention are viable and can be cultured in vitro to recover normal whole plants. The isolated embryo sacs are visible using a stereomicroscope and development can be monitored daily. Within the first week in culture embryo sacs become enlarged as a result of actively growing endosperm. The endosperm proceeds to grow into a large sphere and between the first and second week in culture a proembryo is visible. Embryo development is similar to in vivo developmental patterns and results in an embryo with normal morphology. Such embryos can be germinated by allowing them to remain attached to the endosperm and maternal tissue or can be rescued and germinated separately.

The unfertilized egg cell or zygote contained within the isolated embryo sac is transformed with a foreign gene. Alternatively, an embryo sac containing a later stage in the development of the plant, such as a 2-cell, 4-cell or 8-cell embryo, is transformed with a foreign gene. Yet another alternative is transformation of isolated sperm cells with a foreign gene. The transformed sperm cells are then used to deliver the foreign gene to the egg cell during in vitro fusion to form a zygote.

Transformation of gametes, zygote, embryo or endosperm can be accomplished with any of a variety of methods including microinjection, electroporation, particle bombardment or Agrobacterium. For example, sperm cells are isolated and transformed with a foreign gene by electroporation. An isolated embryo sac containing an unfertilized egg is incubated with the transformed sperm cells. Fusion of a transformed sperm cell with the egg cell produces a transformed zygote that is cultured in vitro to recover uniformly transformed plant which is capable of transmitting the foreign gene to progeny produced by sexual reproduction. Alternatively, a nucleus is isolated from a transformed sperm cell and fused with an egg nucleus to produce a transformed zygote that is cultured in vitro to recover a transformed plant.

The developing endosperm in isolated embryo sacs can be targeted for transformation, for example by microinjection, in order to evaluate the strength of regulatory sequences, such as a specific promoter, in this tissue. Embryo sacs are isolated from a fertilized plant. Endosperm cells are transformed with a foreign gene and allowed to develop in vitro. The foreign DNA, for example, may be a reporter gene such as GUS operably linked to a promoter to be tested. GUS expression is assayed or quantified by methods well known to the skilled artisan such as Northern blot, PCR or Western blot techniques. See, for example, Ausubel et al. (eds.), CURRENT PROTOCOLS IN MOLECULAR BIOLOGY (Wiley Interscience 1990). Based on the level of expression of the foreign gene in the endosperm a prediction can be made as to the whether the selected regulatory sequence will drive sufficient expression of the foreign gene to modify the phenotype of the seed.

Any plant species can be transformed by the claimed method. A particularly preferred plant for transformation by the claimed method are cereals, such as maize. The method of the present invention can be used to circumvent self-incompatibility or species barriers to sexual reproduction. In a plant that exhibits self-incompatibility, pollen tube growth is inhibited. As a consequence, sperm cells are not delivered to the egg sac. Similarly, interspecific hybrids may not be produced due to incompatibility between pollen and stigma. Fusion of sperm and egg cells in an isolated embryo sac circumvents incompatibility between pollen and stigma. Microinjection can be used to introduce a transformed sperm cell or a nucleus isolated from a sperm cell, into the egg. Techniques known to those skilled in the art, using electrical or chemical stimuli, can be used to promote fusion between sperm and egg. See Kranz et al., *Sexual Plant Reproduction* 4: 12–16 (1991) and Deprez et al., *Plant Cell Reports* 14: 204–209 (1995). Further, combinations of these methods such as microinjection of sperm cells into the embryo sac along with fusion-promoting compounds can be used.

A preferred method for introducing foreign DNA into the zygote contained within the isolated embryo sac is microinjection. Embryo sacs are isolated from the fertilized plant. Foreign DNA, for example a reporter gene such as GUS operably linked to a promoter which drives expression in the embryo or plant, is injected into the zygote, which progresses though normal embryogeny and develops into a plant. GUS expression is assayed or quantified by methods well known to the skilled artisan such as histochemical or fluorimetric assays, Jefferson et al., *EMBO J.* 6: 3902–3907 (1987), or by techniques such as Northern blot, PCR or Western blot, as described by Ausubel et al., supra.

Expression Vectors

Expression vectors typically include at least one genetic marker that allows transformed cells to be either recovered by positive genetic selection or screening. However, selectable or screenable markers are not absolutely required in the present invention because gamete, zygote or embryo transformation produces homogeneously transformed T0 plants. Consequently, plants recovered following transformation are simply screened for the transgenic trait.

Alternatively, the expression vector may comprise a selectable or screenable marker. Many of the commonly used positive selectable marker genes for plant transformation were isolated from bacteria and code for enzymes that metabolically detoxify a selective chemical agent which may be an antibiotic or a herbicide. Other positive selective marker genes encode an altered target which is insensitive to the inhibitor.

The most commonly used selectable marker gene for plant transformation is the neomycin phosphotransferase II (nptll) gene, isolated from Tn5, which when placed under the control of plant regulatory signals confers resistance to kanamycin. Fraley et al., *Proc. Nat'l Acad. Sci. U.S.A.* 80: 4803 (1983). Another commonly used selectable marker is the hygromycin phosphotransferase gene which confers resistance to the antibiotic hygromycin. Vanden Elzen et al., *Plan Mol. Biol.* 5: 299 (1985). Additional positive selectable marker genes of bacterial origin that confer resistance to antibiotics include gentamycin acetyl transferase, streptomycin phosphotransferase, aminoglycoside-3'-adenyl transferase and the bleomycin resistance determinant. Hayford et al., *Plant Physiol.* 86: 1216 (1988); Jones et al., *Mol. Gen. Genet.* 210: 86 (1987); Svab et al., *Plant Mol. Biol.* 14: 197 (1990); Hille et al., *Plant Mol. Biol.* 7: 171 (1986).

Other positive selectable marker genes for plant transformation are not of bacterial origin. These genes include mouse dihydrofolate reductase, plant 5-eno/pyruvylshikimate-3-phosphate synthase and plant acetolactate synthase. Eichholtz et al., *Somatic Cell Mol. Genet.* 13: 67 (1987); Shah et al., *Science* 233: 478 (1986); Charest et al., *Plant Cell Rep.* 8: 643 (1990).

Other common selectable marker genes for plants confer resistance to herbicidal inhibitors of glutamine synthetase. European Patent application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyltransferase gene is provided in European application No. 0 242 246 to Leemans et al. De Greef et al., *Bio/Technology* 7: 61 (1989), describe the production of transgenic plants that express chimeric bar genes coding for phosphinothricin-acetyl-transferase activity.

Another class of marker genes for plant transformation requires screening of presumptively transformed plant cells rather than direct genetic selection of transformed cells for resistance to a toxic substance such as an antibiotic. These genes are particularly useful to quantify or visualize the spatial pattern of expression of a gene in specific tissues and are frequently referred to as reporter genes because they can be fused to a gene or gene regulatory sequence for the investigation of gene expression.

Commonly used genes for screening presumptively transformed cells include β-glucuronidase (GUS), β-galactosidase, luciferase, and chloramphenicol acetyltransferase. Jefferson, *Plant Mol. Biol. Rep.* 5: 387 (1987); Teeri et al., *EMBO J.* 8: 343 (1989); Koncz et al., *Proc. Nat'l Acad. Sci. U.S.A.* 84: 131 (1987); De Block et al., *EMBO J.* 3: 1681 (1984). Another approach to the identification of relatively rare transformation events has been use of a gene that encodes a dominant constitutive regulator of the *Zea mays* anthocyanin pigmentation pathway. Ludwig et al., *Science* 247:449 (1990).

A gene encoding GFP can also be utilized as a screenable marker. Co-pending U.S. application Ser. No. 60/016,345, now WO97/41228, incorporated herein by reference, describes strategies for reducing the cellular toxicity of GFP. For example, the gene encoding GFP can be operably linked to an inducible promoter so that GFP can be transiently expressed and transformed cells identified. Alternatively, the gene encoding GFP can be operably linked to a signal sequence for targeting to an organelle or subcellular compartment for secretion to the apoplast where GFP is not toxic to the cell. Signal or targeting sequences for localization in an organelle or subcellular compartment include, but are not limited to chloroplast, peroxisomal., mitochondrial., cell wall, secretion or endoplasmic reticulum retention sequences. GFP can also be modified to replace hydrophobic amino acids with hydrophilic ones thereby reducing the aggregation of the protein and its potential toxicity. Crameri et al., *Nature Biotechnol.* 14: 315–319 (1996).

Oxidative stress can be ameliorated by transforming cells containing GFP with an enzyme that serves as an oxygen scavenger. Such enzymes are well known in the art. For example, genes encoding the enzyme superoxide dismutase (SOD) may protect against the primary oxidative stresses associated with GFP fluorescence. Balzan et al., *Proc. Nat Acad. Sci.* 92: 4219–4223 (1995). Other enzymes involved in the oxidative stress response, such as ascorbate peroxidase or glutathione S-transferase, could help mitigate secondary effects in the cell. Conklin, *Plant Physiol.* 109: 203–212 (1995).

More specifically, oxidative stress can be ameliorated by transforming cells with a DNA construct carrying genes encoding GFP and SOD. Alternatively, the gene encoding GFP can be fused in frame to the gene encoding SOD. Cells transformed with this DNA construct produce a fusion protein that cause the cells to fluoresce in the presence of UV-blue light and express SOD activity.

The toxicity of GFP in transformed plants can be eliminated by excising the screenable marker gene following detection of transformed cells or sectors. The FLP/FRT system is used in conjunction with GFPm as a visible viable marker for FRT excision. The FLP/FRT system has been demonstrated in maize suspension cells using GUS expression as an indicator of FRT excision. Lysnik et al., *NAR* 21: 969–975 (1993). For example, plant cells are bombarded with a DNA construct containing the GFP gene flanked by FRT sequences as well as a foreign or agronomic gene of interest. The GFP gene may be operably linked to a constitutive promoter or an inducible promoter. In addition, the GFP gene may be operably linked to a signal sequence. Stable transformants are detected by means of screening for GFP. Transgenic cells are placed on a medium and bombarded a second time with a FLP recombinase construct. Cells are monitored periodically under UV to blue illumination to detect loss of GFP expression. Cells that no longer express GFP are recovered and analyzed for expression of the foreign or agronomic gene. Agronomically useful transgenic plants are thereby produced that do not contain a marker gene.

The sensitivity of the screening method can be further increased by placing two marker genes between the FRT sequences. For example, cells are bombarded with a DNA construct containing the bar gene encoding phosphinothricin acetyl transferase (PAT) and GFP genes flanked by FRT sequences and a foreign or agronomic gene. Stable transformants are recovered on bialaphos-containing medium and positive GFP-expression is confirmed. The transformed cells are then bombarded with FLP. The cells are then grown for 2–6 weeks with no selection until clear GFP-null sectors can be identified. These sectors can be transferred onto bialaphos/chlorophenol red multiwell test plates to confirm bialaphos sensitivity (i.e., within 3 to 5 days). Cells that no longer express GFP or PAT are recovered and analyzed for expression of the foreign or agronomic gene. This permits recovery of agronomically useful transformants without any marker genes in the final product.

Likewise, the Ac/Ds system of maize can also be used in transgenic plants to excise the screenable marker gene that is transformed together with a foreign or agronomic gene. Mobilization of Ac and/or Ds has been demonstrated in diverse plants such as tomato, tobacco and Arabidopsis. Yoder et al., in TOMATO TECHNOLOGY 189–198 (Alan R. Liss, Inc. 1987); Yoder et al., U.S. Pat. No. 5,225,341; Baker et al., *EMBO J* 6: 1547–1554 (1987); Lawson et al. *Mol. Gen. Genet.* 245: 608–615 (1994). Likewise, the cre/lox recombinase system from bacteriophage P1 could also be used in conjunction with GFP. Excision of transgenes in plants using the cre/lox system was first demonstrated in tobacco. Odell et al., *Mol. Gen. Genet.* 223: 369–378 (1990); Dale & Ow, *Proc. Nat'l Acad. Sci. U.S.A.* 88: 10558–10562 (1991). Similar to the FLP and Ac systems described above, GFP expression provides an efficient, easily scorable phenotype for monitoring excision.

GFP is detected in transformed plant cells by conventional fluorescence detection methods. The transformed cells or tissue are screened for the presence of GFP protein by means of illuminating the cells with UV to blue light and screening for the presence of green fluorescence.

Compound and dissecting microscopes are fitted with appropriate filter combinations for fluorescent protein excitation. Illumination with UV-blue light is required for visualization (excitation around the absorption maximum of 395 nm or around the minor peak at approximately 475 nm for GFP. A hand-held lamp for benchtop work also permits good visualization. Cut-off filters or bandpass filters between the fluorescing tissue and the viewer (i.e. around the intermediate objective or the eyepieces of the microscope, or hand-held in front of the eyes if working on the benchtop) greatly reduces background autofluorescence from the tissue. This cut-off or bandpass filter permits light between 500–550 nm to reach the viewer. Useful filters and wavelengths are not restricted to those described above, and further generic description of the optical characteristics of this system are available. Heim et al., *Currently Biology* 6: 178–182 (1996).

An expression vector is constructed wherein a DNA sequence encoding a foreign protein is operably linked to DNA sequences that regulate gene expression. See, for example, Gruber et al. (1993), supra. The gene encoding a foreign protein may be operably linked to a constitutive promoter such as the nos or CaMV 35S promoters. An, *Plant Physiol.* 81: 86 (1986); Kay et al., *Science* 236: 1299 (1987). Alternatively, the foreign gene is operably linked to a regulatable promoter such as heat shock promoters, hormone-inducible promoter or light-inducible promoters associated with the small subunit of the RuBP carboxylase and LHCP gene families. Ainely et al., *Plant Mol. Biol.* 14: 949 (1990); Yamaguchi-Shinozaki et al., loc. cit. 15: 225 (1990); Kuhlemeier et al., *Plant Cell* 1: 471 (1989).

The gene encoding a foreign protein may be expressed in a tissue-specific or developmentally regulated manner. For example, the gene may be operably linked to a promoter which is specifically expressed in pollen, root or seed. For example, see Albani et al., *Plant Mol. Biol.* 16: 501 (1991);, Depater et al., loc. cit. 18: 161 (1992); and Knutzon et al. *Proc. Nat'l Acad. Sci. U.S.A.* 89: 2624 (1992).

Mitotic stability can be achieved using plant viral vectors that provide epichromosomal replication. An alternative and preferred method of obtaining mitotic stability is provided by the integration of expression vector sequences into the host chromosome.

Transformation Methods

Biological and physical plant transformation protocols are available.

Agrobacterium-mediated Transformation

The most widely utilized method for introducing an expression vector into plants is based on the natural transformation system of Agrobacterium. See, for example, Horsch et al., *Science* 227: 1229 (1985). *Agrobacterium tumefaciens* and *A. rhizogenes* are plant- pathogenic soil bacteria which genetically transform plant cells. The Ti and Ri plasmids of *A. tumefaciens* and *A. rhizogenes,* respectively, carry genes responsible for genetic transformation of the plant. See, for example, Kado, *Crit. Rev. Plant. Sci.* 10: 1 (1991). Descriptions of Agrobacterium vector systems and methods for Agrobacterium-mediated gene transfer are provided by Gruber et al., supra, Miki et al., supra, and Moloney et al., *Plant Cell Reports* 8: 238 (1989).

Direct Gene Transfer

Several methods of plant transformation, collectively referred to as direct gene transfer, have been developed as an alternative to Agrobacterium-mediated transformation. Microprojectile-mediated; sonication; liposome or spheroplast fusion; direct uptake of DNA into protoplasts using $CaCl_2$ precipitation, polyvinyl alcohol or poly-L-ornithine; and electroporation of protoplasts and whole cells are described, supra.

Promoters

Inducible Promoters

Exemplary inducible promoters that can be utilized in the instant invention include that from the ACE1 system which responds to copper (Mett et al. *PNAS* 90: 4567–4571 (1993)); In2 promoter from maize which responds to benzenesulfonamide herbicide safeners (Hershey et al., *Mol. Gen. Genetics* 227: 229–237 (1991), and Gatz et al., loc. cit. 243: 32–38 (1994)) or Tet repressor from Tn10 (Gatz et al., ibid. 227: 229–237 (1991)). A promoter that responds to an inducing agent to which plants do not normally respond can be utilized. An exemplary inducible promoter is the inducible promoter from a steroid hormone gene, the transcriptional activity of which is induced by a glucocorticosteroid hormone. Schena et al., *Proc. Nat'l Acad. Sci. U.S.A.* 88: 10421 (1991).

Tissue-specific or Tissue-Preferred Promoters

Exemplary tissue-specific or tissue-preferred promoters that can be utilized in the instant invention include a seed-preferred promoter such as that from the phaseolin gene (Murai et al., *Science* 23: 476–482 (1983), and Sengupta-Gopalan et al., *Proc. Nat'l Acad. Sci. USA* 82: 3320–3324 (1985)); a leaf-specific and light-induced promoter such as that from cab or rubisco (Simpson et al., *EMBO J.* 4: 2723–2729 (1985), and Timko et al., *Nature* 318: 579–582 (1985)); an anther-specific promoter such as that from LAT52 (Twell et al., *Mol. Gen. Genet.* 217: 240–245 (1989)); a pollen-specific promoter such as that from Zm13 (Guerrero et al., *Mol. Gen. Genet.* 224: 161–168 (1993)); and a microspore-preferred promoter such as that from apg (Twell et al., *Sex. Plant Reprod.* 6: 217–224 (1993)).

Constitutive Promoters

Exemplary constitutive promoters that can be utilized in the instant invention include the promoters from plant viruses such as the 35S promoter of CaMV (Odell et al., *Nature* 313: 810–812 (1985)) and the promoters from such genes as rice actin (McElroy et al., *Plant Cell* 2: 163–171 (1990)); ubiquitin (Christensen et al., *Plant Mol. Biol.* 12: 619–632 (1989) and Christensen et al., *Plant Mol. Biol.* 18: 675–689 (1992)); pEMU (Last et al., *Theor. Appl. Genet.* 81: 581–588 (1991)); MAS (Velten et al., *EMBO J.* 3: 2723–2730 (1984)) and maize H3 histone (Lepetit et al., *Mol. Gen. Genet.* 231: 276–285 (1992) and Atanassova et al., *Plant Journal* 2(3): 291–300 (1992)).

The ALS promoter, a XbaI/NcoI fragment 5-prime to the *Brassica napus* ALS3 structural gene (or a nucleotide sequence that has substantial sequence similarity to said XbaI/NcoI fragment), represents a particularly useful constitutive promoter. The ALS promoter is described in co-pending U.S application Ser. No. 08/409,297, now issued U.S. Pat. No. 5,659,026, which is incorporated herein by reference.

Signal Sequences For Targeting Proteins to Subcellular Compartments

Transport of GFP or other proteins to a subcellular compartment such as the chloroplast, vacuole, peroxisome, glyoxysome, cell wall or mitochondrion, or for secretion into the apoplast, is accomplished by means of operably linking the nucleotide sequence encoding a signal sequence to the 5-prime and/or 3-prime region of a gene. Targeting sequences at the 5-prime and/or 3-prime end of the structural gene may determine, during protein synthesis and processing, where the encoded protein is ultimately compartmentalized. The presence of a signal sequence directs a polypeptide to either an intracellular organelle or subcellular compartment or for secretion to the apoplast.

Exemplary signal sequences that can be utilized in the instant invention include chloroplast signal sequences (Becker et al., *Plant Mol. Biol.* 20: 49 (1992)); mitochondrial signal sequences (Close, P.S., Master's Theses, Iowa State University (1993)); the barley alpha amylase 1 signal sequence (Knox et al., *Plant Mol. Biol.* 9: 3–17 (1987)); the barley lectin vacuole signal sequence (Lerner et al., *Plant Physiol.* 91: 124–129 (1989)); the endoplasmic reticulum retention signal (Fontes et al., *Plant Cell* 3: 483–496 (1991)); the sweet potato sporamin vacuole signal sequence (Matsuoka et al., *Proc. Nat'l Acad. Sci.* 88: 834 (1991)); the consensus peroxisome signal sequence (Gould et al., *J. Cell Biol* 108: 1657 (1989)); and the pea glutathione reductase mitochondrial and chloroplast signal sequence (Creissen et al., *Plant J.* 2: 129 (1991)).

EXAMPLE 1

Isolation of Unfertilized and Fertilized Embryo Sacs from Maize

Plants of *Zea mays* L. (cultivar CV129) were grown to maturity in growth rooms at the University of Alberta. At anthesis, pollen was collected by shaking the tassels over a tray. The collected pollen was used immediately for hand-pollination.

Plants used for cob production were placed in a pollen-free environment by removing plants from the pollen-producing rooms prior to silk emergence. The plants were emasculated, washed to remove any surface pollen and maintained in a pollen-free room for cob development. Emerging cabs were bagged to prevent any indiscriminate pollination.

Embryo sacs containing unfertilized egg cells were isolated from plants having silks measuring approximately 6 cm in length. The length of the silk is not critical., however, to isolation of viable embryo sacs. As long as the silk is not pollinated it can grow to any length including from 1 to 40 cm in length. Silk length depends on such factors as maize genotype or growth conditions.

Embryo sacs containing fertilized eggs cells were also isolated from plants having silks measuring 6 to 10 cm in length. Once again, however, silk length is not critical to isolation of viable embryo sacs. Plants were removed from the pollen-free room and hand-pollinated with fresh pollen. Cobs were subsequently bagged and the plants were placed in a growth chamber for fertilization to occur. Fertilized embryo sacs were isolated at 16 or more hours after pollination. However, the duration between pollination and embryo sac isolation can be reduced. If plants with shorter silks are sued or if the husk leaves are pulled back to expose the silks close to the ovules before applying pollen, fertilized embryo sacs can be isolated as soon as 3–5 hours after pollination.

Unfertilized or fertilized embryo sacs were isolated by removing husks and silks from the cobs. The cobs were cut transversely into approximately 3 cm segments and the segments were surface sterilized for 10 minutes in 70% ethanol followed by three rinses in sterilized, distilled and deionized water. Ovaries were removed and mounted for sectioning.

Figure 1B:
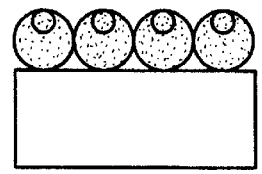
Figure 1C:
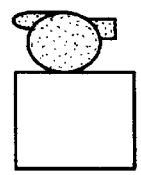

Specimen blocks for use in the microtome were surface sterilized in 70% ethanol for 10 minutes. The blocks were placed in a row in a laminar flow hood. After evaporation of the alcohol, a thin layer of a fast-acting adhesive, "Quick Set 404" (Locktite Corporation, Newington, Conn.), was applied to the top of each block and the ovaries were placed in the proper position. The ovaries were removed in pairs, with two or three pairs placed on each block. The ovaries were placed with their adaxial surface up and perpendicular to the long axis of the specimen block as shown in FIG. 1.

Figure 2A:
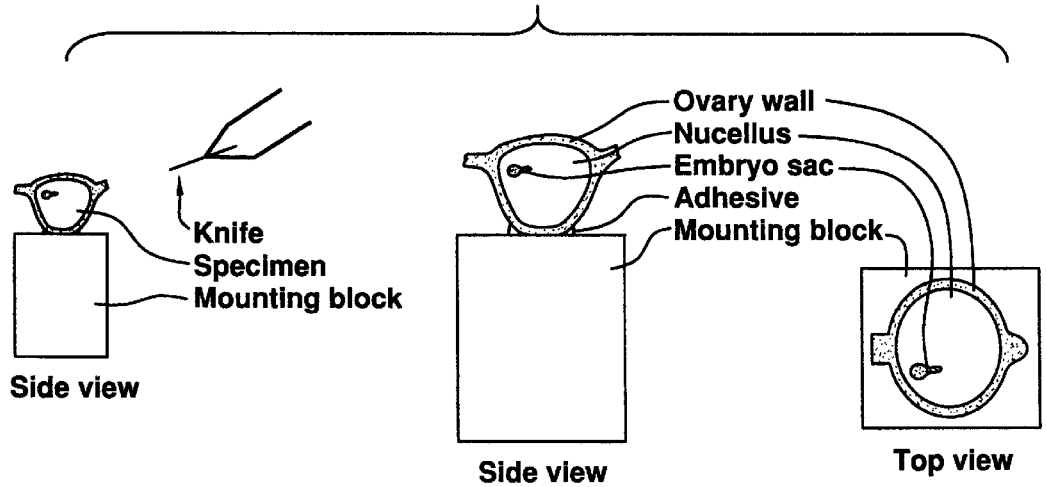
FIGS. 2A–2B present the method for isolation of plant embryo sacs using the Vibratome: (a) components and (b) methodology.
Figure 2B:
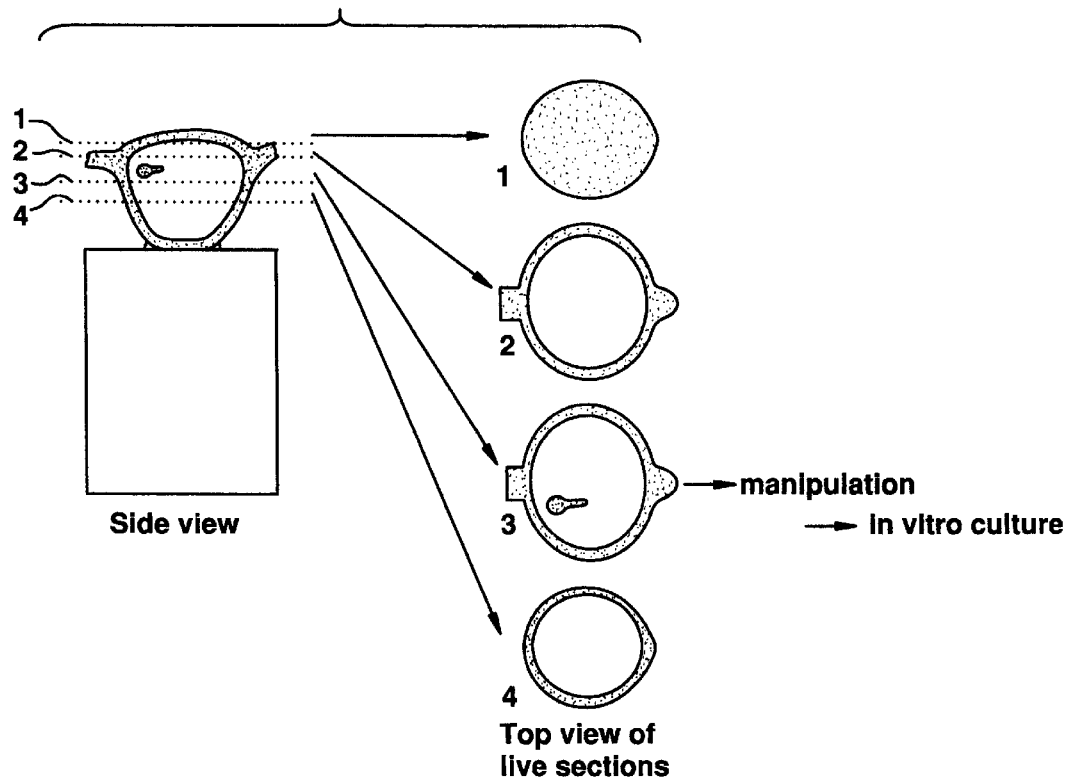

The blocks with the attached ovaries were placed in the Vibratome (Technical Products International., St. Louis, Mo.) with the stylar ends of the ovaries facing the blade as shown in FIG. 2. The blade was positioned above the ovaries and the specimen block was raised to begin sectioning. The ovaries were sectioned at a thickness of 200 to 400 $\mu$m. The first block was serially sectioned in 200 $\mu$m increments from the adaxial surface of the ovaries. Every section was then observed to determine the approximate distance of the embryo sac from the surface. Once the approximate distance of the embryo sac from the surface was determined, sectioning was commenced with the goal of slicing on either side of the embryo sacs but not through them. Thinner sections may improve embryo sac visibility but result in damage to many embryo sacs. Thicker sections result in more intact embryo sacs but with reduced resolution, due to the thickness of the supporting nucellus. Section thicknesses of 250 to 300 $\mu$m routinely produce numerous, viable embryo sacs with acceptable visibility. The sections containing the embryo sacs were collected and placed on a modified MS medium with 0.4 mg/L L-asparagine, 0.1 mg/L 6-benzylaminopurine (BAP) and 15% sucrose, pH 5.8. Murashige et al., *Physiol. Plant* 15: 473 (1962); Campenot et al., *Amer. J. Bot.* 79: 1368 (1992).

The sections were assessed by observing both sides using a stereomicroscope with basal illumination. A section can be easily manipulated by grasping the ovary wall with fine forceps. Intact embryo sacs were placed with their most visible side facing upward for microinjection.

EXAMPLE 2

Microinjection of Maize Zygotes in Isolated Embryo Sacs

Figure 3:
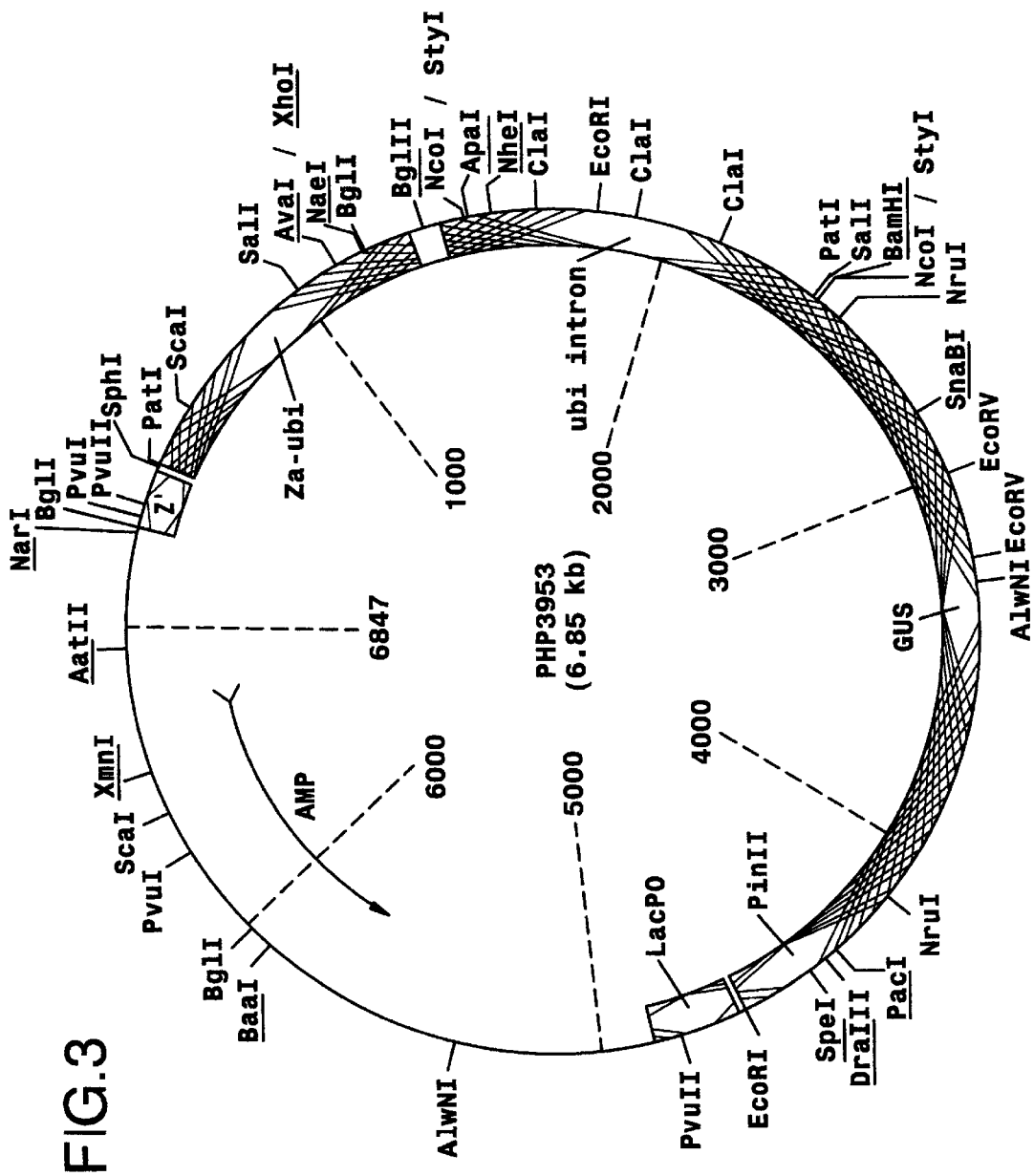
FIG. 3 presents a map of plasmid PHP3953 which carries a gene encoding β-glucuronidase (GUS) for detection of transformed plant cells.

Embryo sacs containing zygotes were isolated as described supra. Maize zygotes in isolated embryo sacs were transformed with plasmid PHP3953 which is shown in FIG. 3. Plasmid PHP3953 carries the GUS structural gene operably linked to the maize ubiquitin (Ubi-1) promoter. Plasmid DNA (100 $\mu$g) was vacuum-dried in Tris-EDTA buffer and dissolved in 0.5 ml milli-Q water. The resulting preparation was divided into 10 ml aliquots and stored at $-20°$ C. until use.

Microinjection pipettes were pulled from borosilicate tubing (1.0 mm×0.75 mm, Sutter Instrument Co.) on a micropipette puller (P-97, Sutter Instrument Co.), bevelled to a tip diameter of 1 to 5 mm with a pipette grinder (BV-10, Sutter Instrument Co.) and autoclaved. After being loaded with plasmid using a microloader (Eppendorf), the microinjection pipette was connected to a Transjector 5246 (Eppendorf). The injection unit of the Transjector was mounted on a MMN-1 three-dimensional manipulator (Narishige) on a Stemi SV11 Stereomicroscope (Zeiss). The angle between the injection pipette and the section was about 45°. The microscope that supports the micromanipulator and injection unit was housed in a laminar flow hood.

The tip of the injection micropipette was brought to the surface of sections by means of a micromanipulator. The tip of the injection micropipette was brought just above the target cells, either the zygote or the central cell. Penetration of a cell was achieved using an hydraulic joystick. Injection volume was adjusted with injection pressure and injection time to about 1 pl. Approximately 100 to 120 embryo sacs can be injected per hour.

GUS activity was determined 5 days after microinjection using a standard GUS histochemical staining protocol. Jefferson, R. A., *Plant Mol. Biol. Rep.* 5: 387 (1987). By that time, endosperm growth was apparent. The embryo sacs were incubated in a petri dish containing a solution comprised of 0.1 M phosphate buffer (pH 7.0), 10 mM EDTA, 0.5 mM potassium ferricyanide, 0.5 mM potassium ferrocyanide, 0.1% triton-X 100 and X-gluc (1 mg/ml) for 30 min under vacuum. The embryo sacs were transferred to an incubator at 37° C. Specimens were examined with the stereomicroscope one hour after incubation.

Histochemical sections from GUS-positive embryo sacs were fixed in glutaraldehyde to determine the cellular location of GUS expression in the embryo sacs. The embryo sacs were fixed overnight in 2% glutaraldehyde. After dehydration in alcohol, the specimens were embedded in Spurr's resin and examined with a brightfield or differential interference contrast microscope. Spurr, A.R., *J. Ultrastruct. Res.* 26: 31 (1969).

Within one week of culture approximately 71% of the isolated embryo sacs produced endosperm. The remaining embryo sacs which failed to develop endosperm only rarely produced an embryo. Embryos developed in approximately 60% of the embryo sacs that produced endosperm.

GUS was detected in approximately 10% of the microinjected embryo sacs 5 days after microinjection of the zygote with PHP3953. The GUS-positive embryo sacs were blue in color. Microscopic analysis of GUS-positive embryo sacs revealed that both zygotes and endosperm appear to be transformed.

Figure 4:
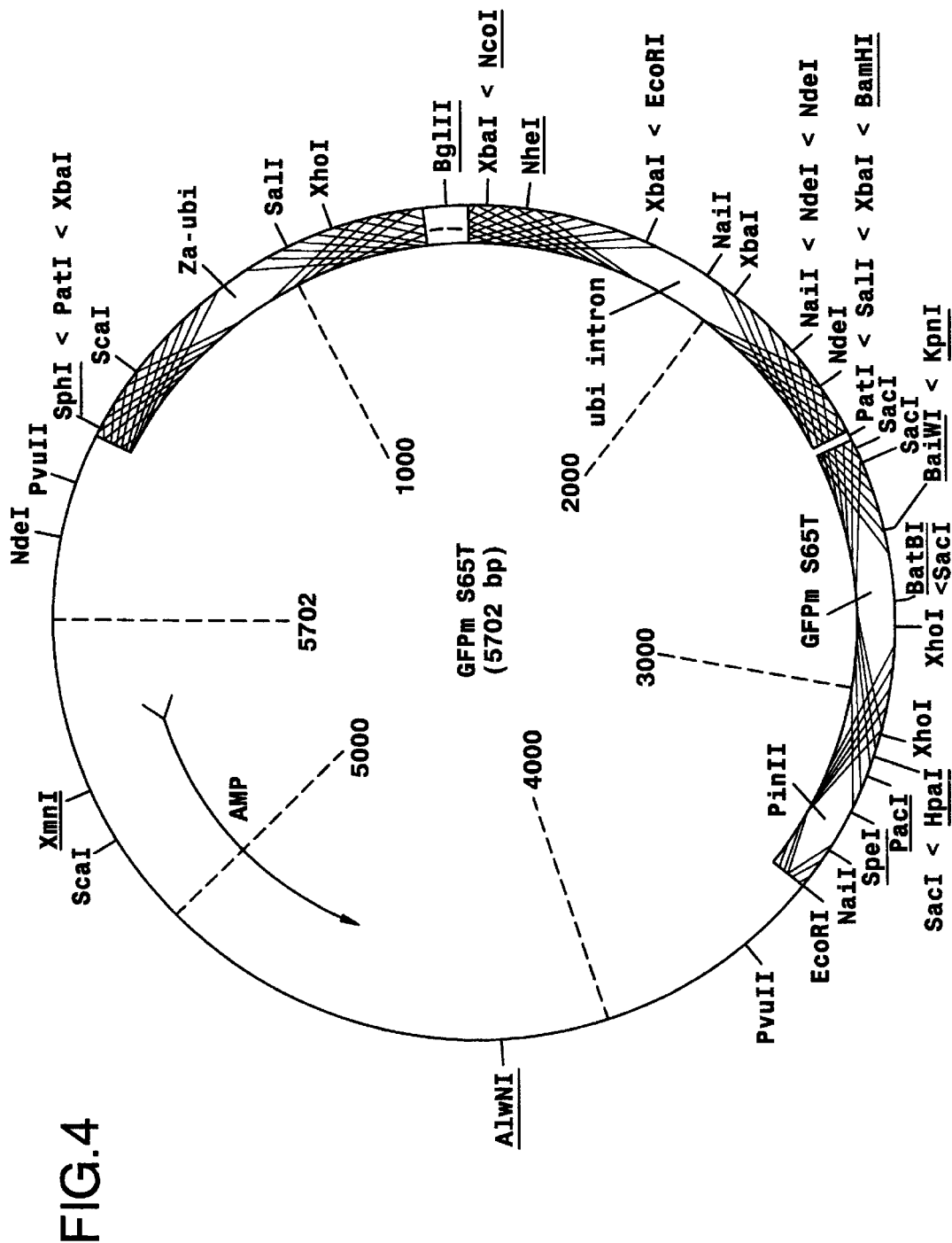
FIG. 4 presents a map of plasmid PHP8088 which carries the GFP gene for detection of transformed plant cells.
Figure 5:
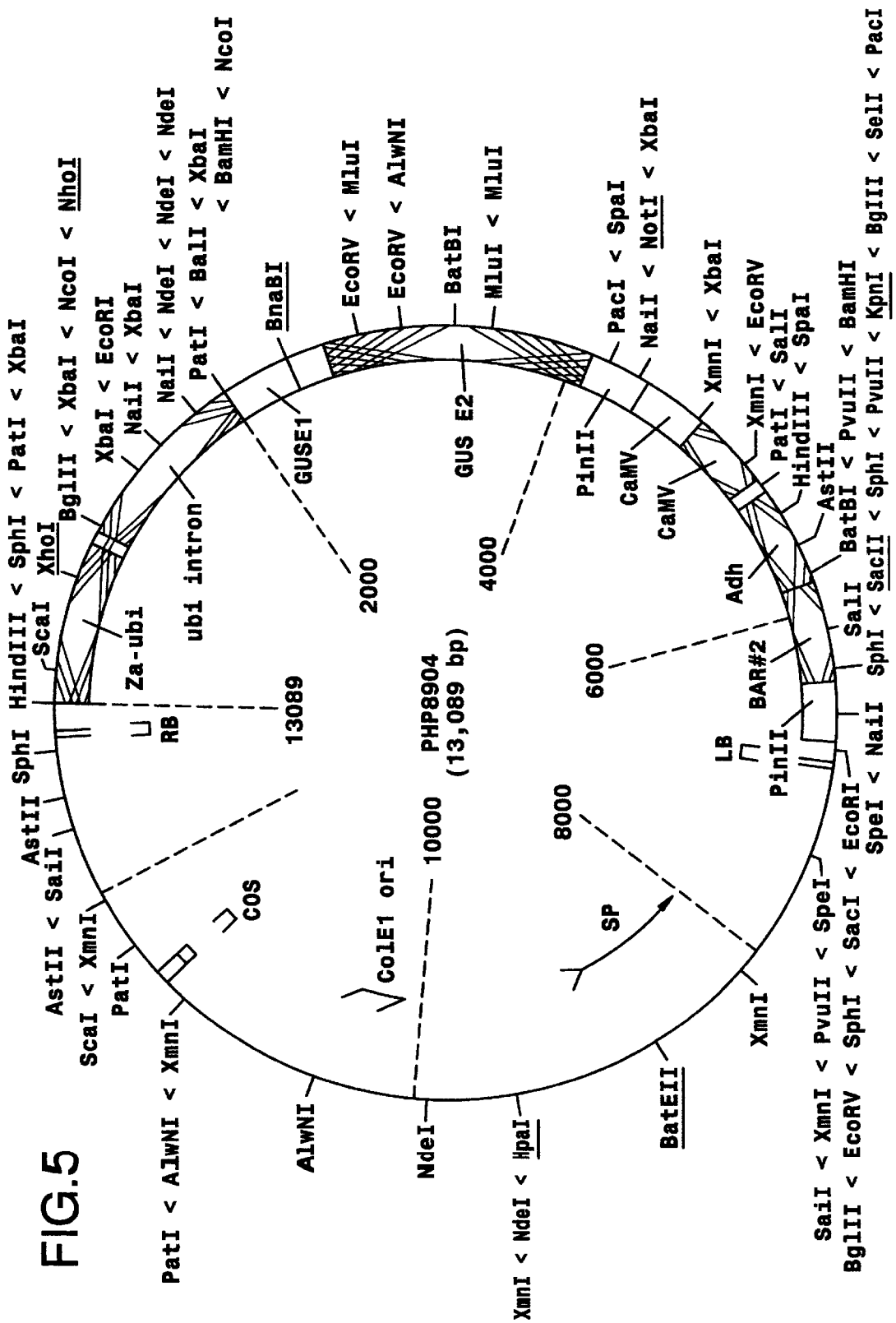
FIG. 5 presents a map of plasmid PHP8904 which is a pTOK246-based vector with the origin of replication of pBR322, a spectinomycin resistance gene and the T-DNA borders.

Using a similar microinjection method and DNA concentration, plasmid PHP8088 is injected into zygotes. Plasmid PHP8088 is shown in FIG. 4 and carries the GFP structural gene operably linked to the maize Ubi-1 promoter. The embryo sacs are screened for detectable GFP with a Carl Zeiss microscope containing a lamp housing with a 75W xenon burner (38-00-53) equipped with a high Q interference exciter filter and a green barrier filter. A fiber optic gooseneck is utilized for scanning petri dishes for GFP-containing cells.

EXAMPLE 3

Recovery and Characterization of Transgenic Plants Produced from Transformed Zygotes Following microinjection of zygotes with PHP3953, embryo sacs were cultured at 25° C. for 5 days in the dark on modified MS medium containing 0.4 mg/L L-asparagine, 0.1 mg/L 6-benzylaminopurine (BAP) and 15% sucrose at pH 5.8. Campenot et al., *Amer. J. Bot* 79: 1368 (1992). Endosperm enlargement was observed after 5 days in culture.

Embryo sacs were then transferred to modified MS medium containing 0.4 mg/L L-asparagine and 10% sucrose at pH 5.8 and no BAP. Following incubation for another 5 days in the dark, embryos were transferred to modified MS medium containing 0.4 mg/L L-asparagine and 3% sucrose at pH 5.8 and no BAP. When young shoots were approximately 1.5 cm long they were exposed to light.

Five days after exposure to light, root tips measuring 1 to 2 cm in length were excised from each seedling for histochemical assay of GUS activity. After excision of root tips seedlings were transferred to a nutrient solution at pH 6.5. Zhang et al., *Plant Physiol.* 94: 577 (1990).

Roots excised from microinjected plants and control plants were incubated in the GUS assay mixture at 37° C. under aseptic conditions. Samples were examined after several hours of incubation with a Stemi SV11 Stereomicroscope (Zeiss). Intact roots from control plants were light brown in color with no evidence of GUS activity. Roots from control plants were squashed under a cover slip and observed under the Zeiss compound microscope. No GUS activity was observed in the root tissue including the cortex and procambium.

GUS activity was detected in the roots excised from plants recovered from embryo sacs microinjected with PHP3953. Three cases of transformants were observed; specifically, blue colored cells were observed in (1) the cortex, (2) the procambium, and (3) the cortex and procambium. None of the transgenic plants obtained through microinjection of zygotes exhibited abnormalities.

EXAMPLE 4

Isolation of *Zea mays* Sperm Cells

Three discontinuous Percoll gradients were prepared for each gram of pollen collected. The Percoll was filter sterilized through a sterile 10 cc syringe with a Millex-GS filter. This filter was placed on the end of the syringe together with a 18G1/2 needle. The discontinuous gradients were made in 15 ml corex test tubes with round bottoms. Approximately 2 to 3 ml of sterile 30% Percoll in Gal-Mes buffer (0.55 M D-galactose; 2 mM 2-(N-morpholino)ethanesulfonic acid; pH 6.7)) was placed in each corex tube. (Sufficient 30% Percoll must be in the tube to avoid disturbing the pellet during sperm cell removal.)

Approximately 2 to 3 ml of sterile 15% Percoll in Gal-Mes buffer (pH 6.7) was carefully placed on top of the 30% Percoll. The sperm cells were found at the interface of the 30% and 15% Percoll. Finally, 2 ml of sterile 10% Percoll in Gal-Mes buffer (pH 6.7) was placed on top of the 15% Percoll. The 10% Percoll was required to remove some of the smaller particles from the sperm cells.

Pollen was collected in a flat tray at anthesis by shaking the tassels. The collected pollen was utilized immediately to avoid desiccation. The pollen grains were separated from the anthers by means of a soft paint brush; the tray was gently shaken during this process.

Fresh pollen was separated by collecting the fresh pollen on the surface of 80 μm nylon mesh. Only 2 to 3 grams of freshly collected pollen was placed on the 5-inch square piece of nylon mesh in order to increase the efficiency of separation. The mesh was shaken gently so that the wrinkled pollen that is not fresh was removed. The fresh pollen collected on the surface of the mesh was placed in a petri dish which was then inserted into a hydration chamber.

The pollen was hydrated for no more than 20 minutes in a covered glass jar containing water in the bottom. The pollen was then osmotically disrupted in a 50 ml Erlenmeyer flask containing 15 ml of Gal-Mes buffer per gram of pollen. The flask was shaken for approximately 20 minutes. Under these conditions the pollen grains burst releasing sperm cells. This mixture was filtered through a 40-mm stainless steel mesh filter with suction to reduce filtering time in order to separate intact pollen and debris from the sperm cells.

A 10 ml syringe with a 18G1/2 needle was used to deliver the filtrate to a discontinuous Percoll gradient as described above. The sperm cells appeared as a smooth white/yellow band at the boundary between the 15% and 30% Percoll layers. The sperm cells were collected with a sterile pipette and placed in a sterile conical tube. Fresh sterile Gal-Mes (pH 6.7) was added to the sperm cells in a ratio of at least 2 ml of gal-MES per ml of sperm cell solution. Following mixing the tubes were centrifuged at 3000 g for 10 minutes and the sperm cells pelleted at the bottom of the tube. The sperm cells were resuspended in Gal-Mes buffer (pH 6.7) at the desired concentration. One gram of maize pollen yielded approximately 3 to 4 million sperm cells using the method described above.

EXAMPLE 5

Transformation of Sperm Cells and Delivery of Foreign Gene to the Egg Cell

Maize sperm cells are isolated from freshly collected pollen according to the method described supra. Final resuspension is performed in 10% Gal-Mes buffer (pH 6.7). Cells are diluted to approximately $2.0 \times 10^6$ cells per ml and 150 ml placed in a 0.4 cm gap electroporation cuvette. KCl is added to a final concentration of 75 mM together with a rhodamine dextran solution (50 µl of a 15 mg per ml stock solution). The suspension then is subjected to electroporation at 250 V and 250 µF and then incubated at room temperature for 10 min to allow resealing of the cell membranes. The presence of the rhodamine label is detected by both conventional and confocal laser microscopy.

The sperm cells are transformed with a vector that carries one or more foreign genes of interest as well as a detectable marker gene. For example, the vector may carry a gene encoding GFP. Alternatively, the vector may carry a fluorescent label. Sperm cells transformed with the vector are separated from non-transformed cells, for example, by flow cytometry and cell sorting. The fusion of sperm and egg cells is facilitated by means of electrical or chemical stimuli. See Kranz et al., supra and Deprez et al., supra.

EXAMPLE 6

Isolation of Nuclei from Transformed Sperm Cells

Sperm cells are isolated and transformed with a foreign gene as described, supra. Transformed sperm cells are suspended in 1 ml Gal-Mes buffer (pH 6.7) and vortexed following addition of 9 ml of 2 mM Mes (ph 6.7) and 0.1 mM KNO$_3$ to rupture the plasma membrane. The osmolarity of the suspension was reestablished by addition of 2 ml 50% galactos in 2 mM Mes (ph 6.7). The mixture containing nuclei and cell debris is loaded on Percoll gradients containing 70, 50 and 30% Percoll in Gal-Mes buffer (pH 6.7). The gradients are centrifuged at 2,000×g for 15 min. Sperm nuclei are collected at the interface between the 50 and 70% Percoll layers, washed with 5 ml Gal-Mes buffer and centrifuged at 1,000×g for 10 min. Pellets containing sperm nuclei are resuspended in 100 ml Gal-Mes buffer. Isolated sperm nuclei are introduced into egg of isolated embryo sacs by microinjection.

EXAMPLE 7

Use of Agrobacterium for Zygote Transformation

Embryo sacs containing zygotes are isolated as described supra. Maize zygotes in isolated embryo sacs are transformed using *Agrobacterium tumefaciens* strain LBA4404. See Hiel et al., *The Plant Journal* 6: 271–282 (1994). For Agrobacterium-mediated transformation of maize, supervirulent plasmids similar to those described by Hiel et al., supra and Ishida et al., supra are used. For example, the backbone of PHP8904 is a pTOK246-based vector with the origin of replication of pBR322, a spectinomycin-resistance gene and the T-DNA borders. See Ishida et al., supra.

Two plant expression units encoding GUS and phosphinothricin-acetyl-transferase (PAT) enzymes are cloned between the right and left border sequences. The first expression unit consists of the maize ubiquitin promoter and the ubiquitin intron; the uidA gene interrupted within the structural gene by a potato catalase intron; and the potato 3" pin II sequence. Christensen et al., *Plant Mol. Biol.* 18: 675–689 (1992); Jefferson et al., *EMBO J.* 6: 3901–3907; Vancanneyt et al., *Mol. Gen. Genet.* 2290: 245–250 (1990); An et al., *Plant Cell* 1: 115–112 (1989).

The second expression unit contains the double 35S promoter; the omega prime (O") 5-prime sequence; the adhl intron; the bar structural gene; and the pin II 3-prime sequence. Close, P., Ph.D. Dissertation, Iowa State University; Gallie et al., *Nucl. Acid Res.* 15: 3257–3273 (1987); Dennis et al., loc. cit. 12: 3983–3990 (1984); and White et al., ibid. 18: 1062 (1990).

Agrobacterium is grown and used in a manner similar to that described in Ishida et al., supra. LBA4404 (PHP8904) is grown for 3 days on YP medium (5 g/l yeast extract, 10 g/l peptone, 5 g/l NaCl, 15 g/l agar, pH 6.8) supplemented with 50 mg/l spectinomycin. Bacteria are collected with a loop from the solid medium and resuspended. For Agrobacterium treatment of isolated embryo sacs, the bacteria are resuspended in the modified MS-based medium used for zygote culture. The concentration of Agrobacterium used for infection and co-cultivation may need to be varied. Infection is initiated by placing the nucellar sections in the Agrobacterium suspension. After about 30 minutes the sections are removed from the liquid and placed on solid zygote culture medium with no antibiotics for the co-cultivation period. It is understood in the art that high densities and long co-cultivation can injure maize cells. Thus, a range of Agrobacterium concentrations from $10^5$–$10^{10}$ cells/ml and a range of co-cultivation periods from a few hours to 3 days are tested with the nucellar sections containing the embryo sacs.

In this manner, the optimal conditions for DNA introduction and zygote survival and development can be found. After the co-cultivation period, the maize tissue is transferred onto zygote culture medium with antibiotics such as 250 mg/l cefotaxime or 100 mg/l carbenicillin. Embryo and plant development continue on antibiotic-containing media. Plants are assayed for the presence and expression of foreign genes such as uidA and PAT using methods described supra. Reciprocal crosses are made between non-transgenic plants and TO plants identified as transgenic. Alternatively, transgenic plants are self-pollinated in order to pass the transgenic trait to progeny.

EXAMPLE 8

Microinjection of Sperm Cells Into Isolated Embryo Sacs

Unfertilized maize embryo sacs were isolated according to the method described in Example 1. Maize sperm cells were isolated according to the method described in Example 4. Sperm cells were microinjected into exposed embryo sacs by inserting the micropipette just above (chalazal to) the egg apparatus according to the method described in Example 2. The egg cells were clearly visible and in many cases the 2 synergids could also be seen. The volume of fluid injected was adjusted to 250–300 pL and each injection contained 2 sperm cells.

Following microinjection, the embryo sacs were cultured as described in Example 3. Endosperm development was observed in 5 days after microinjection. The endosperm was 1.5 mm in length 14 days after microinjection. Microscopic observation of the stained samples revealed that the embryo sacs microinjected with sperm cells developed fully cellular endosperm. Additionally, embryo sacs microinjected with sperm cells contained developing embryos in the micropylar portion of the embryo sac. These embryos underwent normal tissue and organ development.

To determine ploidy level, microinjected embryo sacs were embedded in paraffin or plastic by Campenot et al., A. J. Bot 79(2):1368–1373 (1992). DNA content was determined based on quantitative microphotometry described by Mogensen, H. L. and Holm, P. B., *Plant Cell* 7:487–494 (1995). Specimens were fixed in 95% ethanol and glacial acetic acid (3:1) for 30 min. After dehydration in 95% ethanol for 30 min. and in absolute ethanol for 3 min., specimens were stained in 1 µg/mL-1', 6-diamidino-2 phenylindole (DAPI) for 1 h and mounted with Aquamount. Fluorescence intensity was measured using an Axiovert 135 inverted microscope (Zeiss) equipped with UV light from a 100 watt Hg/Xe-arc lamp, excitation filter 330–380 and barrier filter BA420 and an intensified charge coupled device (CCD) camera (Paultek Imaging). Fluorescence images were digitized and stored using a Macintosh Quadra 950 computer equipped with a Quickcapture frame grabber board (Data Translation). Fluorescence intensity was analyzed using NIH Image (1.56).

Quantitative analysis of ploidy level by microphotometry revealed that the unfertilized embryos microinjected with sperm cells according to the method described supra produced embryos that were 2N and endosperm that was 3N. Accordingly, microinjection of unfertilized embryo sacs with sperm cells according to the method described supra resulted in normal embryo and endosperm development.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

All publications and patent applications mentioned in this specification are indicative of the level of skill of those in the art to which the invention pertains. All publications and patent applications are herein incorporated by reference to the same extent as if each individual publication or patent application were specifically and individually indicated to be incorporated by reference in its entirety.

What is claimed is:

1. A method for producing a transformed maize plant, comprising the steps of (a) isolating an embryo sac from a maize plant;

(b) introducing an expression vector carrying a foreign gene into the zygote or embryo in said embryo sac; and then (c) recovering a transformed maize plant from said zygote or embryo.

2. The method of claim 1, wherein the foreign gene comprises an excisable system.

3. The method of claim 1, wherein the foreign gene comprises a selectable marker.

4. A method for producing a transformed maize plant cell, comprising the steps of (a) isolating an embryo sac from a maize plant; and (b) introducing an expression vector carrying a foreign gene into the zygote or embryo in said embryo sac to form a transformed cell.

5. The method of claim 4, wherein the foreign gene encodes a selectable marker.

6. The method of claim 5 wherein the foreign gene further comprises a signal sequence.

\* \* \* \* \*